US005665380A

United States Patent [19]
Wallach et al.

[11] Patent Number: 5,665,380
[45] Date of Patent: Sep. 9, 1997

[54] LIPID VESICLE FUSION AS A METHOD OF TRANSMITTING A BIOLOGICALLY ACTIVE MATERIAL TO A CELL

[75] Inventors: Donald F. H. Wallach, Hollis; Carole Varanelli, Chester, both of N.H.

[73] Assignee: Micro-Pak, Inc., Wilmington, Del.

[21] Appl. No.: 420,324

[22] Filed: Apr. 11, 1995

Related U.S. Application Data

[63] Continuation of Ser. No. 169,422, Dec. 17, 1993, abandoned.

[51] Int. Cl.$^6$ .............................. A61K 9/127; A61K 9/38
[52] U.S. Cl. ..................... 424/450; 428/402.2; 514/44; 514/8
[58] Field of Search ................ 424/450; 428/402.2; 514/44, 8

[56] References Cited

U.S. PATENT DOCUMENTS

| | | |
|---|---|---|
| 4,217,344 | 8/1980 | Vanlerberghe et al. . |
| 4,241,046 | 12/1980 | Papahadjopoulos et al. . |
| 4,247,411 | 1/1981 | Vanlerberghe et al. . |
| 4,772,471 | 9/1988 | Vanlerberghe et al. . |
| 4,789,633 | 12/1988 | Huang et al. . |
| 4,855,090 | 8/1989 | Wallach . |
| 4,895,452 | 1/1990 | Yiournas et al. . |
| 4,911,928 | 3/1990 | Wallach . |
| 4,917,951 | 4/1990 | Wallach . |
| 5,032,457 | 7/1991 | Wallach . |
| 5,147,723 | 9/1992 | Wallach . |
| 5,160,669 | 11/1992 | Wallach et al. . |
| 5,260,065 | 11/1993 | Mathur et al. . |

FOREIGN PATENT DOCUMENTS

| | | |
|---|---|---|
| 0356340 | 8/1989 | European Pat. Off. . |
| WO 92/06192 | 10/1991 | WIPO . |

OTHER PUBLICATIONS

Wilson et al. "The Introduction of Poliovirus RNA into Cells via Lipid Vesicles" (Liposomes) *Cell*, vol. 17, pp. 77–84 (1979).

Fraley et al. "Introduction of Liposome–encapsulated SV40 DNA into Cells" *J. Biol. Chem.*, vol. 255, pp. 10431–10435 (1980).

Amselem et al. "Fusion of Sendai Virus Negatively Charged Liposomes as Studied By Pyrene–Labelled Phopholipid Liposomes" *Biochimica et Biophysica Acta*, vol. 860, pp. 301–313 (1986).

Ostro, M.J. "Liposomes" *Scientific American* pp. 102–111 (1987).

Mannino et al. "Liposome Mediated Gene Transfer" *BioTechniques*, vol. 6, pp. 682–690 (1988).

Stegmann, et al. "Membrane Fusion Activity of Influenza Virus. Effects of Gangliosides and Negatively Charged Phospholipids in Target Liposomes" *Biochemistry*, vol. 28, pp. 1698–1704 (1989).

Curti, Crit. Rev. Oncol. Hematol., 1993, 14:29–39.

Jain, Scientific American, 1994, 271(1):58–65.

New Scientist, 1995.

13 Biotechnology Law Report 289.

Zwierzina, Stem Cells, 1993, 11:144–153.

Marshall, Science 1995, 269:1050.

Marshall, Science, 1995, 270:1751.

Orkin et al., Report and Recommendations of the Panel to Assess the NIH Investment in Research on Gene Therapy, 7 Dec. 1995.

*Primary Examiner*—Frank C. Eisenschenk
*Attorney, Agent, or Firm*—Lahive & Cockfield, LLP

[57] ABSTRACT

A method for transmitting a biologically active material to a cell is provided. The method involves encapsulating the material to be transmitted in a paucilamellar non-phospholipid carrier vesicle which does not lyse cells upon fusion with cells, delivering the carrier vesicle to a location proximate to the cell, allowing the non-phospholipid bilayer of the carrier vesicle to fuse with the membrane of the cell and allowing the encapsulated material to diffuse into the cell. The method can be used to transmit a variety of biologically active materials to cells either in vitro or in vivo. The method provides a means for transmitting a biologically active material directly to the cytoplasm of a cell. Upon fusion with a cell, material associated with the bilayers of the non-phospholipid vesicle becomes incorporated into the outer membrane of the cell. Accordingly, a method for transmitting bilayer-associated material to a cell is also provided.

30 Claims, 1 Drawing Sheet

LIPID VESICLE FUSION AS A METHOD OF TRANSMITTING A BIOLOGICALLY ACTIVE MATERIAL TO A CELL

This application is a continuation of application Ser. No. 08/169,422 filed on Dec. 17, 1993, now abandoned, Entitled: METHOD OF TRANSMITTING A BIOLOGICALLY ACTIVE MATERIAL TO A CELL. The contents of all of the aforementioned applications are expressly incorporated by reference.

BACKGROUND OF THE INVENTION

The present invention features a method of transmitting biologically active materials into cells. More particularly, the present invention features a method of encapsulating a biologically active material in a non-phospholipid vesicle, delivering the vesicle to a cell, allowing fusion between the vesicle and the cell and allowing the biologically active material to diffuse into the cell, thereby transmitting the biologically active material into the cell. The lipid vesicle protects the encapsulated material from extracellular inactivation and, by fusing to the outer membrane of the target cell, delivers the encapsulated material directly into the cytoplasm of the cell. Upon fusion with the cell, material associated with the bilayer of the non-phospholipid vesicle is incorporated directly into the target cell membrane. Accordingly, the present invention also features a method of transmitting bilayer-associated material to a cell.

The transmission of biologically active materials to cells is an essential component of a wide range of therapies. Such therapies include supplying a cell with a protein having a necessary enzymatic activity, providing a new DNA molecule to a cell (gene therapy), immunizing a subject against a foreign protein (vaccination), immunizing a subject against a foreign protein by introducing the gene encoding the protein (gene vaccination) and inhibiting the production of a protein in a cell by providing the cell with a nucleic acid molecule which is antisense to mRNA encoding the protein or otherwise interfering with the mRNA encoding the protein. While the introduction of a biologically active material into a cell is often desirable, there are several obstacles to overcome in order to accomplish this. Transmission of a biologically active material to a cell involves transferring the material from an extracellular site to an intracellular site while maintaining the activity of the material and not damaging the target cell. The phospholipid bilayer that comprises much of the outer membrane of a cell prohibits the indiscriminate entry of materials into the cell. Although certain hydrophobic molecules can passively diffuse through the outer membrane into the cell cytoplasm, most materials encountered by a cell cannot freely enter the cell. Transporter proteins, which form "channels" through the cell membrane, allow passage of certain specific molecules, usually small molecules, into the cell (e.g., ion channels). Cells also express surface receptors, generally in the form of integral membrane proteins, which bind specific ligands and allow their entry into the cell. Molecules which bind to specific cell-surface receptors generally enter the cell via receptor-mediated endocytosis. Other extracellular material can be taken up by a cell by non-specific endocytosis (e.g., pinocytosis). However, materials which enter the cell via an endocytic pathway generally merge with lysosomal vesicles which contain degradatory enzymes. Thus, materials entering the cell by this route are often destroyed or altered. Additionally, materials may be destroyed prior to entry into a cell. In the body, extracellular substances are subject to inactivation and/or degradation by many different mechanisms if they are not protected in some way from such a fate.

A variety of approaches have been taken to introduce biologically active materials into cells, but most of these approaches have restrictions, such as limits as to types of materials which can be transferred, which limit their usefulness. For example, nucleic acid, such as DNA, can be introduced into cells by numerous transfection techniques, many of which perturb the cell membrane chemically (e.g., calcium phosphate precipitation, DEAE-dextran, lipofection) or electrically (e.g., electroporation). Some of the chemical-mediated transfection techniques (such as lipofection, in which DNA is complexed with cationic lipids) likely involve endocytic uptake of the DNA. While these techniques are useful for introducing nucleic acid into a cell, they are not applicable to many other types of materials. Another limitation of many known approaches for transmitting materials into cells is that they are not applicable to in vivo situations, thereby requiring that the target cell be available in vitro. For example, many of the aforementioned DNA transfection techniques are useful in vitro but are not transferable to in vivo situations. Another type of technique, microinjection, can be used to introduce different types of materials into the cell cytoplasm or nucleus but is technically tedious and is limited in the number of cells which can be modified. Another approach involves using viruses, such as retroviruses, to introduce materials into cells. Viral-mediated transfer can be performed in vivo but primarily is useful for introducing DNA into cells and may not be useful for other types of materials, and, even for DNA, has limited capacity (e.g., size restrictions on the length of DNA that can be transferred). Techniques which permit transmission of materials to cells in vivo are limited and may not allow for targeting of the material to a specific cell type, which is usually desired, thus leading to the need for large systemic dosages of the material.

A delivery system which allows transmission of a variety of a biologically active materials to cells either in vivo or in vitro, protects the materials from inactivation, both extracellularly prior to delivery and intracellularly after delivery and which allows for targeting of the material to specific cells would be highly desirable for many therapeutic applications. One approach in developing such a system is to design a carrier vehicle which can carry and protect, and target if necessary, the biologically active material and which can mediate entry of the material into the cell. A possible carrier vehicle for delivering materials to a cell is a lipid vesicle. Lipid vesicles are substantially spherical structures made of materials having a high lipid content in which the lipids are organized in the form of lipid bilayers. Unilamellar vesicles have a single lipid bilayer surrounding an amorphous central cavity which can encapsulate an aqueous volume. Unilamellar vesicles can be prepared as either large unilamellar vesicles (LUVs; diameter greater than about 1 µ) or small unilamellar vesicles (SUVs; diameter less than about 0.2 µ). Multilamellar vesicles (MLVs) have many onion-like shells of lipid bilayers. Because of their high lipid content, MLVs have use for carrying certain small lipophilic molecules but have a low carrying capacity for aqueous material. Paucilamellar vesicles (PLVs) have about two-ten bilayers arranged in the form of substantially spherical shells separated by aqueous layers surrounding a central cavity free of lipid bilayers. PLVs can encapsulate both aqueous and hydrophobic material and thus can carry a wide variety of materials.

Unilamellar vesicles composed of a single bilayer of phospholipids and/or glycolipids are the most commonly used lipid vesicles for modeling of cell membrane structures since phospholipids are the primary structural component of natural membranes, including the outer cell membrane. Phospholipid vesicles have been used as carrier vehicles for delivering biologically active materials to cells. However, such vesicles do not fuse with the outer membrane of the cell but rather are generally taken up by cells via endocytosis and enter the lysosomal degradation pathway. Biologically active materials carried by the lipid vesicle may then be destroyed by lysosomal enzymes. Attempts have been made to construct phospholipid vesicles which will avoid this fate. Methods used to circumvent the lysosomal pathway include use of pH-sensitive liposomes, which fuse with endosomal membranes in the acidic environment of the endosome, thereby releasing their contents before exposure to lysosomal enzymes, and incorporation of viral fusion proteins into the phospholipid vesicle to promote fusion of the vesicle with the outer cell membrane, thereby avoiding endocytosis of the vesicle. For reviews of phospholipid vesicle-mediated transfer of materials see Mannino, R. J. and Gould-Fogerite, S., BioTechniques, 6:682 (1988); Litzinger, D. C. and Huang, L., Biochim. et Biophys. Acta, 1113:201 (1992).

The use of phospholipid vesicles as carrier vehicles for delivery of biologically active materials to cells is limited by the necessity to manipulate the vesicles so as to avoid lysosomal destruction of the encapsulated material. Furthermore, phospholipid vesicles can be costly to produce, are not stable in vitro and may not be stable long-term in vivo because of the activity of phospholipases in vivo. An alternative carrier vehicle for delivery of biologically active materials is a paucilamellar non-phospholipid vesicle. Advantages of paucilamellar non-phospholipid vesicles include that they are less costly to produce than phospholipid vesicles, are more stable in vivo than phospholipid vesicles, and have a large carrying capacity for encapsulated material. It has now been discovered that when certain paucilamellar non-phospholipid vesicles are contacted with cells they do not cause lysis of the cells and are not taken up by the cell via endocytosis, but rather fuse with the outer membrane of the cell. Thus, rather than being introduced into the endocytic pathway, and ultimately the lysosomal pathway, material carried by the paucilamellar non-phospholipid vesicle is introduced directly into the cytoplasm of the cell. Additionally, upon fusion the non-phospholipid bilayers of the vesicle are incorporated into the outer membrane of the cell.

Accordingly, an object of the invention is to provide a method of transmitting a biologically active material to a cell using a non-phospholipid vesicle carrier.

Another object of the invention is to provide a method of transmitting a biologically active material to a cell in vivo in a mammal using a non-phospholipid vesicle carrier.

A further object of the invention is to provide a method of delivering a biologically active material directly to the cytoplasm of a cell by fusion of a non-phospholipid vesicle carrying the material with the outer membrane of the cell.

A still further object of the invention is to provide a method of delivering material associated with the bilayers of a non-phospholipid vesicle to the phospholipid outer membrane of a cell by fusion of the non-phospholipid vesicle with the outer membrane of the cell.

These and other objects and features of the invention will be apparent from the following description and claims.

SUMMARY OF THE INVENTION

The present invention features a method of transmitting a biologically active material to a cell, either in vitro or in vivo. A biologically active material is encapsulated in a non-phospholipid vesicle, the vesicle is contacted with a cell, the vesicle is allowed to fuse with the outer membrane of the cell and the biologically active material is allowed to diffuse into the cell, thereby delivering the material encapsulated within the vesicle to the cell. The invention is based, at least in part, on the discovery that certain non-phospholipid vesicles, rather than being taken up by a cell via endocytosis or causing the cell to lyse, will fuse with the outer membrane of the cell when brought to a location proximate to the cell. Upon fusion with the cell, the material encapsulated by the vesicle is free to diffuse into the cell. The method of the invention provides a means of delivering a material encapsulated by the vesicle directly to the cytoplasm of a cell in an active form. Furthermore, fusion of the non-phospholipid vesicle with the cell results in transfer of material associated with the bilayers of the vesicle to the outer membrane of the cell.

The method of transmitting a biologically active material to a cell has the initial step of encapsulating the material in a lipid vesicle. The vesicle functions: 1) to protect the material from extracellular inactivation prior to delivery of the material to the cell; 2) to carry the material to the cell; and 3) to deliver the material into the cell by fusing with the outer membrane of the cell. The primary structural lipids of the bilayers of the lipid vesicles used in the invention are non-phospholipids. The vesicles are paucilamellar vesicles, with about 2–10 lipid bilayers, which provide a large carrying capacity for both aqueous and hydrophobic materials and are more stable than unilamellar vesicles. Methods of manufacturing these vesicles, and the vesicles themselves, are described in more detail in U.S. Pat. No. 4,911,928, U.S. Pat. No. 5,147,723, U.S. Pat. No. 5,032,457, U.S. Pat. No. 4,895,452 and U.S. Pat. No. 5,260,065, the disclosures of which are all incorporated herein by reference. The non-phospholipid vesicles of the invention have the property that the non-phospholipid material forms vesicles which fuse with cells without lysing cells upon contact with cells. Preferred non-phospholipid materials for use in the vesicles include polyoxyethylene fatty ethers having the formula: $R-CO(C_2H_4O)_nH$, where n ranges from 2–4 and R is a hydrocarbon chain selected from the group consisting of cetyl alcohol, stearyl alcohol and oleoyl alcohol or their derivatives. In addition to the non-phospholipid wall-forming material, the vesicles can also contain a sterol, such as cholesterol, a cholesterol-based salt or ester, phytocholesterol, or hydrocortisone. A charge producing agent can also be added to the vesicle. Preferred charge producing agents are those which produce a negative charge, such as dicetyl phosphate, cholesterol hemisuccinate and oleic acid. Positively charged vesicles are not preferred.

A biologically active material which is soluble in an aqueous solution can be encapsulated in the internal aqueous space of a non-phospholipid vesicle during the preparation of the vesicle. The non-phospholipid is blended together with any sterol or other lipophilic additives to form a liquid lipid phase. An aqueous phase is normally formed by heating the hydration liquid, e.g., water, saline or any other aqueous solution which will be used to hydrate the lipid, and the aqueous soluble material to be incorporated into the vesicle. The aqueous phase and the lipid phase are then blended under "shear mixing" conditions to form vesicles. Shear mixing is defined as the mixing of the lipophilic phase with the aqueous phase under turbulent or shear conditions to provide adequate mixing to hydrate the lipid and form lipid vesicles. Shear mixing is achieved by liquid shear which is substantially equivalent to a relative flow rate for the combined phases of about 5–30 m/s through a 1 mm radius orifice. Vesicles can be prepared manually or by use of an apparatus for preparing vesicles such as that described in U.S. Pat. No. 4,895,452. Preferred biologically active materials which are soluble in an aqueous solution and thus can be added to the aqueous phase include nucleic acids, such as RNA and DNA and fragments (e.g., oligonucleotides, ribozymes) and derivatives thereof, proteins and fragments (e.g., peptides) and derivatives thereof, enzymes, enzyme substrates and hydrophilic pharmaceutical agents. A biologically active material which is hydrophobic (i.e., water immiscible) can also be encapsulated in a non-phospholipid vesicle. Oil filled vesicles, e.g., vesicles having their central cavities filled with a water immiscible oily material, may be formed using either the "hot loading" technique disclosed in U.S. Pat. No. 4,911,928 or the "cold loading" technique described in U.S. Pat. No. 5,160,669, the disclosure of which is also incorporated herein by reference. Preferred hydrophobic biologically active materials include steroids and other hormones, lipid-soluble vitamins and hydrophobic pharmaceutical agents.

Following vesicle formation and encapsulation of the biologically active material, the vesicle is brought to a location proximate to the cell to which the material is to be delivered. The cell can be in vitro, such as a cell in a culture medium, or can be a cell in vivo, such as a cell in a mammal. In vitro, the vesicle can be added to the culture medium or other solution containing the cell. In vivo, the vesicle can be introduced, for example, by intravenous, intranasal, intramuscular, subcutaneous, percutaneous, intratracheal or topical administration. The vesicles can be incorporated into sprays, creams, gels or other solutions to aid in their administration by a particular route. Additionally, a targeting molecule can be incorporated into the lipid vesicle which directs the vesicle to a particular cell type. For example, antibodies, viral proteins or ligands which bind cell membrane receptors can be coupled to the lipid vesicle. Coupling can be accomplished, for example, by the method disclosed in U.S. Pat. No. 5,000,960, the disclosure of which is hereby incorporated by reference. A vesicle which contains a targeting molecule is brought to a location proximate to a cell and the targeting molecule is allowed to seek the cell, thereby directing the vesicle to the cell. Upon binding of the target molecule to the target cell, the vesicle fuses with the outer membrane of the target cell, thereby delivering the encapsulated material to the cell.

The composition and concentration of the lipid vesicle used to transmit material is such that the vesicle will fuse with the outer membrane of the cell to which the encapsulated material is to be delivered yet the fusogenic activity of the vesicle is not so great as to lyse the cell. Upon fusion, the lipid bilayers of the vesicle become incorporated into the lipid bilayer of the outer membrane of the cell and the encapsulated material is delivered to the cell by diffusion of the material out of the vesicle and into the cytoplasm of the cell. Thus, the method of the invention provides a means of delivering an encapsulated material directly to the cytoplasm of a cell, thereby avoiding exposure of the material to the degradatory lysosomal pathway, and, additionally, provides a means of delivering material associated with the lipid bilayers of the vesicle (e.g., the non-phospholipids themselves and any other incorporated material) to the outer membrane of the cell.

The method of the invention is useful for a wide range of therapeutic applications. A biologically active material can be transmitted to a cell to stimulate an activity in the cell. For example, a functional protein or a gene encoding a functional protein can be delivered to a cell in which the protein is diminished or absent, thereby stimulating in the cell the functional activity mediated by the protein. Alternatively, a biologically active material can be transmitted to a cell to inhibit an activity in the cell. For example, an antisense nucleic acid or ribozyme can be delivered to a cell to prevent translation of an mRNA into a functional protein, thereby inhibiting in the cell the functional activity mediated by the protein.

DETAILED DESCRIPTION OF THE INVENTION

Figure 1:
FIG. 1 is an freeze fracture electron micrograph of an erythrocyte following fusion of the erythrocyte with non-phospholipid vesicles. The bald areas represent membrane material inserted by the non-phospholipid vesicle into the erythrocyte membrane upon fusion. Magnification=×63,000

The present invention concerns a method of transmitting a biologically active material to a cell. This method is based on the fusion of paucilamellar non-phospholipid vesicles, encapsulating the material to be transmitted, with the outer membrane of the recipient cell. The fusion of a non-phospholipid vesicle to the phospholipid cell membrane is an unexpected finding since there is a large difference in the properties of the phospholipids of the cell membrane and the non-phospholipids used in the vesicles. Phospholipids have a dual carbon chain structure as compared with the single carbon chains used in the non-phospholipid vesicles. The method of the invention involves the steps of 1) encapsulating the material to be transmitted in a paucilamellar non-phospholipid vesicle; 2) delivering the vesicle carrying the material to a location proximate to the cell; 3) allowing the vesicle to fuse with the cell; and 4) allowing the material to diffuse into the cell.

The vesicles used to deliver the biologically active material to a cell are paucilamellar vesicles with about 2–10 lipid bilayers encapsulating said biologically active material. A non-phospholipid material is the primary structural lipid in the bilayers. The non-phospholipid material has the property that it forms vesicles which fuse with cells without lysing cells upon contact with cells. Preferred non-phospholipid materials for use as the primary structural lipid in the bilayers of the vesicle are selected from the group consisting of polyoxyethylene fatty ethers having the formula: R—CO$(C_2H_4O)_n$H where n ranges from 2–4 and R is a hydrocarbon chain selected from the group consisting of cetyl alcohol, stearyl alcohol and oleoyl alcohol or derivatives thereof. The bilayers of the vesicle can further comprise a sterol, e.g., cholesterol, a cholesterol-based salt or ester, phytocholesterol, or hydrocortisone. The bilayers of the vesicle can further comprise a negative charge producing agent, e.g., dicetyl phosphate, cholesterol hemisuccinate and oleic acid. The bilayers of the vesicle can further comprise a phospholipid.

Many different types of biologically active materials can be delivered to a cell. The term "biologically active material" is intended to include substances which themselves provide a functional activity to a cell and substances which stimulate or inhibit an endogenous functional activity within the cell. The functional activity of the substance is maintained upon its delivery to the cell. The non-phospholipid vesicle carrier can be used to deliver either aqueous materials or hydrophobic materials. Examples of hydrophilic materials which can be delivered include: proteins and fragments (e.g., peptide fragments) and derivatives thereof including: peptide hormones such as insulin, calcitonin and glucagon, hypothalmic peptides, pituitary hormones, growth factors such as angiogenic, epithelial and epidermal growth factors, lymphokines such as interleukins and interferons and blood proteins such as hemoglobin and Factor VIII; nucleic acids such as DNA and RNA, including fragments (e.g., oligonucleotides) and derivatives thereof; water-soluble pharmaceutical agents including anti-cancer drugs, immunosuppressive drugs, antiparasitic drags and antibiotics; enzymes; enzyme substrates; and materials which label a cell such as fluorescent dyes, radionucleotides and contrast materials for radiological and NMR diagnoses. Examples of hydrophobic materials which can be encapsulated include hormones such as steroids; lipophilic vitamins; hydrophobic pharmaceutical agents such as cyclosporin A; pheromones; porphyrins and organic pesticides and fungicides. A more complete listing of types of pharmaceutical agents that can be encapsulated in lipid vesicles is included in Gregoriadis, G., ed. *Liposome Technology* (CRC, Boca Raton, Fla.), Vol. 1–3 (1984).

A preferred type of protein is an enzyme which can supply a necessary enzymatic activity to a cell. A preferred type of nucleic acid is a DNA molecule containing a gene encoding a protein to be supplied to the cell in a form such that the gene is transcribed into mRNA and the mRNA is translated into protein, thereby supplying the protein to the cell. Another preferred type of nucleic acid is an antisense nucleic acid, such as an oligonucleotide, which is complementary to an mRNA in the cell and which prevents translation of the mRNA by binding to the mRNA. Yet another preferred type of nucleic acid is a ribozyme, a catalytic RNA molecule which can destroy a target mRNA within the cell. Materials such as pharmaceutical agents, hormones, enzyme substrates and vitamins can be used to stimulate or inhibit a response in a cell. A radioopaque or paramagnetic molecule can be used in order to label a cell, for example so that its location in the body can be detected (e.g., detection of rumor cells).

Once encapsulated into a non-phospholipid vesicle, the biologically active material can be delivered to a cell either in vitro or, preferably, in vivo by delivering the vesicle to a location proximate to the cell. In vitro, the vesicles are brought to a location proximate to the cell by incubating the vesicles with the cells. For example, a cell can be isolated from a subject, a material can be transmitted to the cell in vitro and the cell can then be reintroduced into the subject. In vivo, the vesicles can be administered to a subject (e.g., a mammal) by a route which allows the vesicles to be brought to a location proximate to a target cell. Extracellularly, prior to fusion with the target cell, the vesicle protects the material encapsulated within it from inactivation or degradation as well as from immunological recognition. This is an especially useful aspect when transmitting a protein to a cell since proteins are very susceptible to extracellular degradation and provoke an immune response against the protein.

Possible routes for administering the vesicles in vivo include intravenous, intranasal, intramuscular, subcutaneous, percutaneous, intratracheal and topical administration. For example, vesicles can be administered intravenously, intramuscularly or subcutaneously by injection of the vesicles. Alteratively, vesicles can be administered percutaneously by catheterization, for example, a catheter can be inserted into an artery or vein or a catheter can be inserted into a particular organ or minor to deliver the vesicles to that location. The vesicles can be incorporated into a composition, such as a spray, a cream, a gel or a pharmaceutically acceptable carrier (e.g., an aqueous syringeable saline solution) to allow appropriate in vivo administration.

The vesicle composition and concentration is selected to cause fusion of the vesicles with the cell without causing cell lysis. The fusogenic activity versus toxicity of a vesicle preparation can be tested in vitro in assays as described in the Examples to follow. For example, the effect of the vesicles on erythrocyte membranes can be assessed (see Example 6). Conditions for cell fusion and material transfer can thus be optimized with cells in vitro. The fusogenic activity of vesicles can be modulated by forming the vesicles with a blend of non-phospholipids composed of a highly fusogenic non-phospholipid and a non-fusogenic phospholipid. For example, the fusogenic activity of vesicles containing polyoxyethylene (2) cetyl ether can be downmodulated by incorporating batyl alcohol into the vesicles (see Example 6, Table 4). Formation of blended lipid vesicles is described in U.S. Pat. No. 5,260,065, the disclosure of which is hereby incorporated by reference. Additionally, a vesicle in which the primary wall forming material is non-phospholipid material can further include a phospholipid.

When a material is to be delivered specifically to a particular type of cell but the vesicle is delivered to a location proximate to more than one type of cell (e.g., many in vivo situations), the vesicle can be directed to the target cell of interest by incorporating a targeting molecule into the vesicle. The targeting molecule functions to seek out the target cell of interest and bind to the target cell, thereby directing the vesicle to the target cell. Preferred targeting molecules include antibodies, e.g.monoclonal antibodies, which bind to a surface structure on the target cell of interest, ligands for receptors on the surface of the target cell of interest and vital proteins, e.g. membrane proteins from enveloped viruses, which mediate binding of the virus to a particular cell type. The targeting molecule can be modified such that it can be incorporated into the lipid bilayer of the vesicle. For example, a soluble protein can be provided with a hydrophobic anchor molecule which allows the protein to be tethered to the lipid vesicle. Alternatively, a targeting molecule can be incorporated using a bispecific coupling reagent, such as by the procedure disclosed in U.S. Pat. No. 5,000,960 (previously incorporated by reference). In this procedure, thiocholesterol is first incorporated into the non-phospholipid vesicle and then a coupling reagent which is reactive with sulfhydryl and amino groups is used to crosslink proteins, via their amino groups, to the vesicle, via the sulfhydryl group of thiocholesterol.

When a non-phospholipid vesicle encapsulating a biologically active material contains a targeting molecule, the vesicle can be delivered to a cell by delivering the vesicle to a location proximate to the cell and allowing the targeting molecule to seek the cell. When the cell to which the biologically active material is to be delivered is in vivo, e.g., in a mammal, the vesicle can be delivered to the cell by delivering the vesicle to the bloodstream of the mammal and allowing the targeting molecule to seek the cell.

The method of the invention can be used to deliver biologically active material to virtually any type of cell. The cell can be a mammalian cell. For example, cells to which material can be transmitted include erythrocytes, lymphocytes, fibroblasts, tumor cells, virally-infected cells, epithelial cells, endothelial cells, myocytes, hepatocytes, endocrine cells, neuronal cells, dermal cells, germ cells, oocytes, sperm cells, stem cells, hematopoietic stem cells, embryonic cells, M cells, Langerhans cells and macrophages. Additionally, the cell can be a plant cell. For example, material can be transmitted to a plant cell for bioagricultural purposes, such as to confer resistance to a destructive agent on the plant cell. Additionally, the cell can be a parasitic cell. For example, a pharmaceutical agent which is destructive to a parasite can be transmitted to the parasite.

The method of the invention can be used for many therapeutic applications. In one embodiment of the invention, a biologically active material is delivered to an erythrocyte. Therapeutic uses for transmission of materials to erythrocytes include treatment of sickle cell crises by adjusting the intracellular environment, and treatment of intraerythrocytic parasites, such as the erythrocytic stage of malaria, by delivering anti-parasitic pharmaceutical agents to the erythrocytes. Vesicles can be delivered in vivo to a location proximate to erythrocytes by intravenous administration of the vesicles.

In another embodiment of the invention, a biologically active material is delivered to a lymphocyte. Therapeutic uses for transmission of materials to lymphocytes include treatment of adenosine deaminase deficiency by delivering adenosine deaminase to lymphocytes, prevention of tissue graft rejection by delivering immunosuppresive drugs, such as cyclosporin, to lymphocytes and immunization against a foreign antigen by delivering peptidic fragments of the antigen to B lymphocytes (or other antigen presenting cells). Delivery of peptide fragments to a cell according to the method of the invention will result in delivery of the peptides to the cytoplasm of the cell whereupon the peptides will be transported through the MHC class I processing pathway. Peptides processed and presented in this manner induce a cytotoxic T cell (CTL) response. Thus, the method of the invention can be used to induce a CTL response against a foreign antigen. Vesicles can be targeted to lymphocytes by incorporating a targeting molecule specific for lymphocytes into the vesicle. For example, an anti-CD4 monoclonal antibody could be used to target vesicles to CD4+T lymphocytes. This could be useful for delivering anti-viral agents to HIV-infected CD4+T lymphocytes.

The method of the invention can also be used to deliver materials to cells in the brain. Intranasal administration, such as by a nasal spray, of vesicles encapsulating the material can allow transmission of materials to brain cells via the olfactory pathway. This could be especially useful as a delivery mechanism for pharmaceutical agents which cannot cross the blood-brain barrier.

Other therapeutic applications include introducing the dystrophin protein into muscle cells of patients suffering from muscular dystrophy to alleviate the disease by intramuscular injection of vesicles encapsulating dystrophin. Tumors could also be treated by delivering anti-minor agents, such as chemotherapeutic drugs, to tumor cells by injection vesicles carrying an anti-tumor agent into the tumor.

A still further therapeutic application of the method of the invention is for gene therapy. In recent years, the molecular basis for many inherited disorders has been elucidated and the genes involved in these disorders have been isolated. This has provided the potential for therapeutic treatments based upon supplying a functional gene to a patient having a defect in that gene. The current method of transmitting a biologically active material to a cell can be used to deliver a gene encoding a functional gene product into cells of a patient to restore the activity of that gene in the patient. Some diseases associated with mutations in a known gene which could be treated by gene therapy using the method of the invention are as follows (each disease is followed by the respective gene): sickle cell anemia (β-globin), thalassemia (β-globin), cystic fibrosis (CFTR), Duchenne's muscular dystrophy (dystrophin), adenosine deaminase deficiency (adenosine deaminase), hemophilia A (Factor VIII), hemophilia B (Factor IX) and Tay-Sachs disease (α1-hexosaminidase). An extensive list of genetic disorders which could be treated by gene therapy is included in Antonarakis, *New England J. of Medicine*, 320:153–163 (1981). Furthermore, gene therapy approaches can be applied to acquired disorders as well, for example by introducing into cells of a patient genes encoding gene products which enhance the responsiveness of the patient's immune system. Accordingly, therapeutic or preventive treatments for diseases such as cancer and AIDS could be carded out using the method of the invention for gene therapy. For example, introduction into cells of DNA encoding the HIV gp160 protein can lead to expression of the gp160 protein to elicit immunity to HIV (gene vaccination).

Another aspect of the invention concerns a method of transmitting a material associated with the bilayers of a non-phospholipid vesicle to a cell. Upon fusion with the outer membrane of a cell, the lipid bilayers of the non-phospholipid vesicles used in the invention become incorporated into the outer membrane of the cell. Thus, fusion of a non-phospholipid vesicle with a cell provides a method for transmitting bilayer-associated materials to a cell. Bilayer-associated material includes the non-phospholipids themselves, which are the primary component of the bilayers of the non-phospholipid vesicles, and may include other material such as a sterol, (e.g., cholesterol, a cholesterol-based salt or ester, phytocholesterol, or hydrocortisone), a negative charge producing agent (e.g., dicetyl phosphate, cholesterol hemisuccinate and oleic acid) and/or a phospholipid. Additionally, bilayer-associated material can include molecules which have been incorporated into the non-phospholipid bilayers of the non-phospholipid vesicle. For example, a protein or a fragment (e.g., peptide) or derivative thereof, can be inserted into the bilayer of a vesicle and transmitted to the membrane of a cell by fusion of the vesicle with the cell. Membrane-spanning envelope proteins of myxovirus virus have been incorporated into the non-phospholipid bilayer of non-phospholipid vesicles after fusion of the vesicles with the virus envelope (see U.S. patent application Ser. No. 08/005,008, incorporated herein by reference).

The transmission of non-phospholipid bilayer-associated material to the outer membrane of a cell upon fusion of non-phospholipid vesicles with the cell can be used to alter properties and functions of the target cell. This is based upon the fact that the non-phospholipid bilayers of the vesicle which become incorporated into the outer membrane of the cell have different properties than normal cell membranes, leading to changes in cell permeability and altered active transport mechanisms. For example, excessive fusion of non-phospholipid vesicles with cells decreases the replication of the cells in vitro (see Example 8). Thus, the replication of a cell can be inhibited by targeting the non-phospholipid vesicles of the invention to the cell and allowing the vesicles to fuse with the cell, thereby transmitting the bilayer-associated material to the outer membrane of the cell to a degree which inhibits replication of the cells. For example, minor cells or virally-infected cells can be targeted for fusion with non-phospholipid vesicles using monoclonal antibodies directed specifically against such cells as targeting molecules (e.g., using monoclonal antibodies reactive with a tumor-associated antigen or with a virally-encoded cell-surface protein) to decrease the replication of these

11 cells. Additionally, transmission of bilayer-associated material to a cell can be used to alter signal transduction within a cell in response to an external stimuli (e.g., hormone, growth factor, etc.) by altering the composition of the outer membrane of the cell.

The following examples, which should not be construed as limiting, will more clearly illustrate the invention and its efficacy.

EXAMPLE 1

In this example, a substrate for an enzyme was introduced into avian erythrocytes using a paucilamellar non-phospholipid vesicle carrier. Transmission of the substrate to the cells was determined by measuring the reactivity of the enzyme, present endogenously within the erythrocytes, against the substrate after contacting the vesicles with the erythrocytes.

The chemical 2,2'-azino-bis(3-ethylbenzthiazoline-6-sulfonic acid) (ABTS; Sigma A 1888) was encapsulated in a paucilamellar non-phospholipid vesicle composed of polyoxyethylene (2) cetyl ether (Brij 52; ICI Americas Inc.)/cholesterol/dicetylphosphate (3/1/0.01; M/M/M). ABTS is a substrate for a peroxidase enzyme activity present endogenously in the erythrocytes.

The non-phospholipid vesicles were made using the general procedures set forth in U.S. Pat. No. 4,911,928. Briefly, the lipid components of the vesicle walls were heated to a flowable state (75° C.) and placed in a first syringe (1 ml of lipid in a 10 ml syringe). The aqueous component was also heated (55° C.) and placed in a second syringe (4 ml of ABTS solution in a 10 ml syringe). The two syringes were connected by the stopcock and the materials were pushed back and forth through the stopcock for a minute or two until vesicles were formed (about 60 strokes, cooling every 20 strokes). The preparation was fluid and showed fairly homogenous vesicles upon microscopic examination. A 1:10 dilution of the vesicles were made. The final ABTS concentration was 2 mg/ml. "Blank" non-phospholipid vesicles, in which ABTS was not encapsulated, were also prepared.

Chicken erythrocytes (Vineland Laboratories) were washed twice with phosphate buffered saline. 20 µl of cells were incubated with 2 ml of (a) a 1:10 dilution of ABTS-loaded vesicles, (b) a 1:10 dilution of blank vesicles or (c) unencapsulated ABTS (2 mg/ml). Cells were incubated with the solutions at 37° C. for one hour, then at room temperature for two hours. No cell lysis was apparent upon microscopic examination. The erythrocytes exposed to the non-phospholipid vesicles were more swollen in appearance and had a lighter cytoplasm than cells not exposed to the vesicles.

Following incubation, 200 µl aliquots of each mixture were washed and exposed to 100 µl of hydrogen peroxide (0.3%), which permeates the erythrocyte membrane and initiates the peroxidase reaction inside the cell in the presence of ABTS. Within one half to one hour, cells exposed to ABTS-loaded vesicles displayed a light purple color, indicative of peroxidase activity. In contrast, the cells exposed to either blank vesicles or unencapsulated ABTS remained a brownish-red color, characteristic of methemoglobin present within the cells. The purple color of the cells treated with ABTS-loaded vesicles darkened upon addition of a second 100 µl aliquot of hydrogen peroxide. The detectable peroxidase activity in these cells, as indicated by the purple color, demonstrates that the peroxidase substrate, ABTS, was transferred to the cells upon fusion of the ABTS-loaded vesicles with the cells.

12

EXAMPLE 2

In this example, an enzyme was introduced into arian erythrocytes using a paucilamellar non-phospholipid vesicle carrier. Transmission of the enzyme to the cells was determined by measuring the amount of cell-associated enzymatic activity present after contacting the vesicles with the cells.

The enzyme, horse radish peroxidase (HRP; Sigma P-6782), was encapsulated in paucilamellar non-phospholipid vesicles composed of polyoxyethylene (2) cetyl ether (Brij 52)/cholesterol/oleic acid as described in Example 1. Unencapsulated enzyme was removed by multiple centrifugal washings on dextran density gradients. The last wash was saved. "Blank" non-phospholipid vesicles, without encapsulated enzyme, were also prepared.

A 1:10 dilution of HRP-loaded vesicles was incubated with $2.3 \times 10^6$ chicken erythrocytes (obtained from Vineland Laboratories) at 37° C. for 1 hour. Control erythrocytes were also incubated with (a) a 1:10 dilution of the final wash solution, (b) blank vesicles at equivalent dilution and (c) a 1:10 dilution of blank vesicles made up in a 1:10 dilution of the final wash. At the end of the incubation, the erythrocytes were centrifugally separated from the vesicles. No cell lysis occurred. The cells were disrupted in 100 µl octylglucoside (100 mg/ml), followed by 100 µl substrate (ABTS; 10 mg/ml) and 100 µl $H_2O_2$ (0.3%). The color at 405 nm was read against a standard curve. The results are shown in Table 1.

TABLE 1

Transfer of HRP from Non-phospholipid Vesicles to Avian Erythrocytes

| Conditions | HRP (µg/$10^6$ cells) |
| --- | --- |
| Erythrocytes + blank vesicles | 25[a] |
| Erythrocytes + final wash | 25[a] |
| Erythrocytes + HRP-loaded vesicles | 100[b] |

[a] These values represent the peroxidase activity of hemoglobin
[b] Corresponds to 6.6% transfer or approx. $10^6$ molecules/cell

EXAMPLE 3

In this example, an enzyme was introduced into murine lymphocytes using a paucilamellar non-phospholipid vesicle carrier. Transmission of the enzyme to the cells was determined by measuring the amount of cell-associated enzymatic activity present after contacting the vesicles with the cells.

As described in Example 2, HRP was encapsulated in paucilamellar non-phospholipid vesicles composed of polyoxyethylene (2) cetyl ether (Brij 52)/cholesterol/oleic acid, and unencapsulated enzyme was removed by multiple centrifugal washings on dextran density gradients. The last wash was saved. "Blank" non-phospholipid vesicles, without encapsulated enzyme, were also prepared.

A 1:20 dilution of HRP-loaded non-phospholipid vesicles was incubated with $1.3 \times 10^6$ SP2 myeloma cells (differentiated B lymphocytes) at 37° C. for one hour. As controls, SP2 cells were also incubated with (a) a 1:20 dilution of the final wash of the HRP-loaded non-phospholipid vesicles, (b) a 1:20 dilution of blank non-phospholipid vesicles and (c) a 1:20 dilution of blank non-phospholipid vesicles made in a 1:20 dilution of the final wash. At the end of the incubation period, the SP2 cells were separated from the non-phospholipid vesicles by washing and centrifugation. No cell lysis was observed under these conditions.

The cell pellets were resuspended in 200 μl of octylglucoside (100 mg/ml) to disrupt the SP2 cell membranes. 200 μl of HRP enzyme substrate (ABTS; Sigma; 10 mg/ml) and 200 μl of hydrogen peroxide (0.3%) were added to the disrupted cells. The color produced was read at 405 nm after 30 minutes. The results are shown in Table 2.

TABLE 2

Transfer of HRP from Non-phospholipid Vesicles to SP2 Myeloma Cells

| Conditions | HRP ($OD_{405}$) |
|---|---|
| SP2 cells + blank vesicles | 0.135 |
| SP2 cells + final wash | 0.130 |
| SP2 cells + blank vesicles in wash | 0.120 |
| SP2 cells + HRP-loaded vesicles | 0.306 |

Color development was more than two-fold greater than controls after cells had been incubated with non-phospholipid vesicle-encapsulated HRP. This suggests non-phospholipid vesicle/cell fusion and transfer of enzyme into the target cells of more than $5 \times 10^6$ molecules of HRP/cell. Adhesion of the non-phospholipid vesicle to the cells cannot be fully ruled out by this assay, but is excluded by the DNA transfer experiment described in Example 4.

EXAMPLE 4

In this example, a DNA molecule was introduced into murine fibroblasts using a non-phospholipid vesicle carrier. Transmission of the DNA molecule to the cells was determined by measuring the activity of a protein encoded by the DNA molecule present in the cells after contacting the cells with the vesicles.

Assays which determine the delivery of the contents of a lipid vesicle to the cytoplasm of a target cell must distinguish between real vesicle-cell fusion and either simple adherence of the vesicle to the cell surface or endocytosis of the vesicle without the release of the encapsulated contents. One way of quantitating the cytoplasmic delivery of vesicle contents is to utilize a molecule which will initiate protein synthesis when it is delivered to the cytoplasm in an active form. One such molecule is a DNA plasmid which contains a gene encoding a protein having a measurable enzymatic activity and which contains appropriate regulatory sequences to allow for transcription of the gene and translation of the resultant mRNA into detectable protein. Measurement of the enzymatic activity of the protein present in the cell provides an assessment of the transfer of the DNA into the cytoplasm of the cell The system used in this example is based upon the high-efficiency protein synthesis in mammalian cells resulting from the interaction of T7 promoters with T7 RNA polymerase (A). NIH 3T3 fibroblast cells constitutively expressing T7 RNA polymerase were used. The DNA plasmid introduced into these cells was pEMC-LacZbgAn, which expresses the lac Z gene under the regulation of the T7 promoter. Because transcripts from the T7 RNA polymerase are not 5' capped, the 5' UTR from EMC virus has been engineered into this plasmid to give high efficiency translation. In addition, a poly (A) sequence has been added to the 3' end to enhance mRNA stability.

The plasmid was encapsulated in a non-phospholipid vesicle made of polyoxyethylene (2) cetyl ether (Brij 52)/ cholesterol as described in Example 1. 20 μg plasmid DNA/ml was used for encapsulation (total non-phospholipid=5 ml; encapsulation efficiency was not determined but typically is greater than 35%). Neutral, positively charged and negatively charged non-phospholipid vesicles were tested. Various dilutions of DNA-loaded non-phospholipid vesicles were added to NIH 3T3 cells expressing T7 RNA polymerase endogenously and incubated overnight before the culture medium was changed. A 1:1000 dilution of the non-phospholipid vesicles (equivalent to 0.375 ng of plasmid DNA/well) was used for the experiments described to avoid toxicity due to excessive fusion upon overnight incubation. As a positive control, the cells were also transfected with the same plasmid by a calcium phosphate precipitation technique (at a concentration of 123.33 ng of plasmid DNA/well). As a negative control, free plasmid DNA (at a concentration of 123.33 ng of plasmid DNA/well) was added to the cells. After 48 hours, the cells were assayed for β-galactosidase activity.

The results given below are averages of three separate wells and represent three different experiments. β-galactosidase activity is expressed as $OD_{570}$/well. The results are shown in Table 3.

TABLE 3

Transfer of DNA from Non-phospholipid Vesicles to NIH 3T3 Cells

| Conditions | DNA (molecules/cell) | $OD_{570}$[a] | $OD_{570}$/DNA |
|---|---|---|---|
| Free DNA (123 ng/well) | $1.6 \times 10^6$ | 0.100[b] | $6 \times 10^{-9}$ |
| $CaPO_4$-precipitated DNA (123 ng/well) | $1.6 \times 10^6$ | 0.800 | $5 \times 10^{-8}$ |
| DNA-loaded vesicles (0.375 ng/well total) | $4.3 \times 10^3$ | 0.258 | $6 \times 10^{-5}$ |
| (~0.09 ng/well encaps.) | $~1 \times 10^3$ | — | $2 \times 10^{-4}$ | a Representing β-galactosidase activity
b Essentially background

It should be noted that the total amount of non-phospholipid DNA added per well, which includes both encapsulated and unencapsulated DNA, is greater than 300 times less than the $CaPO_4$ positive control, and greater than 600 times less in terms of encapsulated DNA. Even though present at a much lower concentration than the positive control DNA, the non-phospholipid encapsulated DNA (NPL DNA) is transmitted to the cells during incubation, as indicated by the 2 to 2½ fold increase in β-galactosidase activity present in the cells following incubation of the cells with NPL DNA as compared to the free DNA negative control.

EXAMPLE 5

In this example, oligonucleotides were encapsulated into non-phospholipid vesicles and the encapsulation efficiency was determined.

A mixture of $^{32}$P-guanine-labeled anti-c-myc-5G, unlabeled anti-c-myc, labeled anti-VSV-5G and unlabeled anti-VSV were used for encapsulation. 0.4 ml of polyoxyethylene (2) cetyl ether/cholesterol/dicetylphosphate (3.0/1.0/0.1; M/M/M) was combined using the syringe technique described in Example 1 with 0.5 ml 10 mM Tris HCl, 150 mM NaCl, pH 7.4, containing 20 μg (100,000 dpm) of the antisense mixture. The resulting vesicles were diluted to 4 ml and the vesicles centrifuged on a dextran gradient (20%; 10%; 40 minutes, 40,000 rpm). The bottom of the centrifuge tubes were punctured to elute the tube contents. In all experiments, non-encapsulated oligonucleotides appeared in drops 1–10 and the encapsulated material in fraction 12. The encapsulation efficiencies were 72.4–76.0%.

EXAMPLE 6

In this example, non-phospholipid vesicles of different compositions were assayed for their relative fusogenic activity. Fusogenic activity was assayed by incubating the vesicles with human erythrocytes and examining the effect of the vesicles on the erythrocyte membranes by light microscopy. Various non-phospholipid vesicle formulations were prepared and incubated with 1% citrated human erythrocytes at room temperature and at 37° C. Erythrocyte membranes were monitored microscopically over time (immediately, 1 hour, 2 hours, overnight etc.). It was found that incubation of human erythrocytes with different vesicles led to different qualitative effects on the erythrocyte membranes which could be detected microscopically. The spectrum of the observed effects on the erythrocyte membranes, from the least affected membranes to the most affected membranes, were as follows: 1) round, essentially non-deformed membranes; 2) round, slightly deformed membranes with "hair"-like projections; 3) round, slightly more deformed membranes with "needle"-like and "rod"-like projections; 4) moderately crenated membranes with aggregated membrane particles but without "rod"-like projections; 5) severly crenated membranes with aggregated membrane particles and with "rod"-like and tubular projections; 6) partially lysed membranes and red cell "ghosts"; and 7) rapid lysis with burst membranes. The results are summarized in Table 4.

TABLE 4

Effects of NPL Vesicles of Different Membrane Compositions on Human Erythrocytes

| Composition[a,b] | Appearance/effect |
|---|---|
| Control (isotonic saline) | Round or biconcave |
| POE (3) GMS/Chol/SA | Round or biconcave |
| POE (9) GMS/Chol | |
| POE (2) SE/Batyl Alcohol/Chol/Chol HS | |
| POE (2) CE/Batyl Alcohol/Chol/Chol HS | |
| POE (2) SE/Chol/GMS/SA | |
| Batyl Alcohol/Chol/SA | |
| GDL/Chol | Round with hair |
| GDS/POE (10) SE/Chol | |
| GMS/Egg Lecithin/Chol | |
| Caprol 3 glycerol-1 stearyl/Chol | |
| Caprol 6 glycerol-2 stearyl/Chol | |
| GMS/POE (2) CE/Chol/OA | Round with rods |
| POE (2) SE/Chol/OA | |
| GMS/Chol/Egg Lecithin | Crenated; no rods |
| Caprol 3 glycerol-1 oleoyl/Chol | |
| Caprol 6 glycerol-2 oleoyl/Chol | |
| POE (2) CE/Chol | Crenated with rods |
| POE (2) CE/Chol/DCP | |
| POE (2) CE/Chol/OA | |
| GMO/Chol/SA | Red cell ghosts |
| POE (9) GMS/GMO/Chol/SA | |
| POE (4) LE/GDL/Chol/SA | |
| POE (9) GMO/Chol/SA | |
| POE (10) CE/Chol | Rapid Lysis |
| DMATO/Chol | |
| Linoleamide/Chol/OA | | a Abbreviations: POE — polyoxyethylene; SE — stearyl ether; LE — lauryl ether; CE — cetyl ether; GMS — glyceryl monostearate; GDL — glyceryl dilaurate; GDS — glyceryl distearate; GMO — glyceryl monooleate; Chol. — cholesterol; Chol. HS — cholesterol hemisuccinate; SA — stearic acid; OA — oleic acid; DCP — dicetyl phosphate; DMATO — dimethyl amides of tall oil fatty acids
b 1/100–1/1000 dilution of non-phospholipid vesicles Similar results to those reported in Table 4 were observed when the different non-phospholipid vesicle compositions were incubated with arian erythrocytes.

The fusogenic activity of vesicles of different lipid compositions can be predicted by comparing the effect of the vesicles on erythrocytes membranes to that of POE (2) CE (Brij 52) containing vesicles, which are known to have good fusogenic activity (see Examples 1–4). As shown in Table 4, POE (2) CE-containing vesicles caused crenation of erythrocyte membranes without causing them to lyse or form ghosts. Vesicles which caused no or minimal deformation of the erythrocyte membrane, such as those containing POE (3) GMS and POE (9) GMS as the principal wall-forming material, are predicted to have no or low fusogenic activity, whereas vesicles which caused formation of ghosts or complete lysis of the erythrocytes, such are those containing GMO, POE (9) GMS/GMO, POE (4) LE/GDL, POE (10) CE, DMATO and linoleamide, are likely to be too reactive to be useful for transfer of materials to cells. Preferred vesicles for transmitting materials to cells cause moderate deformation to severe crenation of erythrocyte membranes with rod-like and tubular projections forming from the membranes. These include vesicles composed of POE (2) SE and POE (2) CE. The addition of other components to vesicles formed from these lipids (i.e., blended lipid vesicles) can be used to modulate the fusogenic activity of the vesicle. For example, the addition of batyl alcohol to a POE (2) SE (Brij 72) and POE (2) CE (Brij 52) vesicles reduced the effect of the vesicles on erythrocyte membranes. The erythrocyte assay described in this example can be used to screen non-phospholipid vesicles of different compositions for their fusogenic potential. Vesicles can then be directly tested for their ability to fuse with and deliver a material to a cell by assays such as those described in Examples 1–4.

EXAMPLE 7

In this example, the nature of the erythrocyte deformation process upon fusion with non-phospholipid vesicles was investigated by freeze fracture electron microscopy. Fresh, washed human erythrocytes in phosphate buffered saline were mixed with polyoxyethylene (2) cetyl ether (Brij 52)/cholesterol/oleic acid vesicles, prepared as described in Example 1. The erythrocytes were incubated with the vesicles (about 105 vesicles/cell) for 18 hours at room temperature and then examined by freeze fracture electron microscopy. A representative electron micrograph is shown in FIG. 1. Electron microscopy demonstrated that the rods and tubules were filled with erythrocytic cytoplasm, i.e., were projections of the erythrocyte membrane, rather than being formed merely by the lipid vesicles. Furthermore, the distribution of intramembranous particles—representing erythrocyte transmembrane proteins—was severely altered by the interaction with the vesicles. Instead of a statistical distribution of particles without prominent particle-free domains, the fracture faces of treated erythrocytes exhibit huge "bald" areas that contain few or no intramembranous particles, most of these particles having aggregated into tight clusters. The bald areas range in area from 1 to 3 $\mu^2$, equivalent to 2–6 times the surface area of the non-phospholipid vesicles used. The electron micrographs indicated that upon fusion of the non-phospholipid vesicles with the erythrocyte membrane, material associated with the bilayer of the vesicles was transferred (i.e., inserted into) the outer membrane of the erythrocyte.

The freeze fracture electron microscopy experiments described above were repeated with NIH 3T3 fibroblasts using the same non-phospholipid vesicle composition. Similar results were observed with 3T3 cells, namely large bald patches and aggregated particles were observed, suggestive of fusion of the vesicles with the cellular membrane and transmission of bilayer-associated material to the cellular membrane.

EXAMPLE 8

In this example, the effect of excessive fusion on cell replication were examined by incubating different concentrations of non-phospholipid vesicles with cultured fibroblasts for varying amounts of time and then measuring cell proliferation.

The freeze fracture electron microscopy experiments described in Example 7 indicated that fusion of non-phospholipid vesicles with target cells can create cells which have large portions of the vesicle bilayer inserted into the normal outer cellular membrane. Since the bilayer of the vesicle has different properties than normal cellular membranes and can alter cell permeability and active transport mechanisms, it was examined whether excessive fusion could alter cell replication in vitro.

Increasing amounts of non-phospholipid vesicles were incubated with NIH 3T3 fibroblasts for increasing amounts of time. The effect of cell fusion on the cell membrane was examined visually by light microscopy and the effect on cell replication was determined using a cell proliferation assay. The results are shown in Table 5.

TABLE 5

Effects of Fusogenic Non-phospholipid Vesicles on Cultured Fibroblasts

| Exposure Time | Vesicle Concentration/ml[a] | | |
|---|---|---|---|
| | $2 \times 10^{11}$ | $1 \times 10^{11}$ | $3 \times 10^{10}$ |
| 4.5 hr visual | normal | normal | normal |
| 4.5 hr formazen[b] | 81 | 80 | 95 |
| 8.0 hr visual | normal | normal | normal |
| 8.0 hr formazen[b] | 87 | 97 | 100 |
| 24.0 hr visual | abnormal | normal | normal |
| 24.0 hr formazen[b] | 48 | 97 | 100 | a Computed from particle size and lipid mass for 2 bilayers
b Promega Cell Titer 96 AQ cell proliferation assay. Data expressed as % of controls.

The data show that small increases in vesicle concentration above $3 \times 10^{10}$/ml and increased exposure time of cells to vesicles can lead to excessive fusion which inhibits cell replication. This would be expected from calculations based upon relative surface areas of the cell membranes and the non-phospholipid bilayers. For example, $10^6$ spherical cells with radii of 3–7 microns would have surface areas of $7 \to 20 \times 10^7$ $\mu^2$. Non-phospholipid vesicles are usually prepared at concentrations of about $10^{14}$ particles/ml. For vesicles with 2 bilayers and a radius near 0.25 microns, this corresponds to about $2 \times 10^{13}$ $\mu^2$, a membrane surface area excess of up to $10^6$-fold.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of transmitting a biologically active material to a cell in vitro, comprising the steps of:
   (a) forming a carrier vesicle having about 2–10 lipid bilayers encapsulating said biologically active material, said carrier vesicle being in the form of a paucilamellar lipid vesicle having a non-phospholipid material as the primary structural lipid in said bilayers, said non-phospholipid material being selected from the group consisting of polyoxyethylene fatty ethers having the formula:

$$R-CO(C_2H_4O)_nH$$

where n ranges from 2–4 and R is a hydrocarbon chain selected from the group consisting of cetyl alcohol, stearyl alcohol and oleoyl alcohol or derivatives thereof,
   (b) delivering said carrier vesicle containing said biologically active material to a location proximate to said cell in vitro;
   (c) allowing said lipid bilayer of said carrier vesicle and the membrane of said cell to fuse; and
   (d) allowing said biologically active material to diffuse into said cell.

2. The method of claim 1, wherein said lipid bilayer further comprises a sterol.

3. The method of claim 1, wherein said lipid bilayer further comprises a negative charge producing agent.

4. The method of claim 1, wherein said biologically active material comprises a protein or a fragment or derivative thereof.

5. The method of claim 4, wherein the protein is an enzyme.

6. The method of claim 1, wherein said biologically active material comprises a pharmaceutical agent.

7. The method of claim 1, wherein said cell is an erythrocyte.

8. The method of claim 1, wherein said cell is a lymphocyte.

9. The method of claim 1, wherein said cell is a fibroblast.

10. The method of claim 1, wherein said cell is selected from the group consisting of tumor cells, virally-infected cells, epithelial cells, endothelial cells, myocytes, hepatocytes, endocrine cells, neuronal cells, dermal cells, germ cells, oocytes, sperm cells, stem cells, hematopoietic stem cells, embryonic cells, M cells, Langerhans cells, macrophages, plant cells and parasitic cells.

11. The method of claim 1, wherein said carrier vesicle further comprises a targeting molecule and said step of delivering said carrier vesicle to a location proximate to the cell comprises delivering said carrier vesicle to a location proximate to said cell and allowing said targeting molecule to seek said cell.

12. The method of claim 11, wherein said targeting molecule is an antibody.

13. The method of claim 11, wherein said targeting molecule is a viral protein.

14. The method of claim 11, wherein said targeting molecule is a ligand for a receptor on said cell.

15. The method of claim 1, wherein said biologically active material diffuses into the cytoplasm of said cell.

16. The method of claim 1, wherein said biologically active material stimulates an activity in said cell.

17. The method of claim 1, wherein said biologically active material inhibits an activity in said cell.

18. A method of transmitting a bilayer-associated material to a cell in vitro, comprising the steps of:
   (a) forming a carrier vesicle having about 2–10 lipid bilayers incorporating said bilayer-associated material, said carrier vesicle being in the form of a paucilamellar lipid vesicle having a non-phospholipid material as the primary structural lipid in said bilayers, said non-phospholipid material being selected from the group consisting of polyoxyethylene fatty ethers having the formula:

$$R-CO(C_2H_4O)_nH$$

where n ranges from 2–4 and R is a hydrocarbon chain selected from the group consisting of cetyl alcohol, stearyl alcohol and oleoyl alcohol or derivatives thereof, (b) delivering said carrier vesicle incorporating said bilayer-associated material to a location proximate to said cell in vitro;

(c) allowing said lipid bilayer of said carrier vesicle and the membrane of said cell to fuse; and (d) allowing said bilayer-associated material to be transmitted to the membrane of said cell.

19. The method of claim 18, wherein said lipid bilayer further comprises a sterol.

20. The method of claim 18, wherein said lipid bilayer further comprises a negative charge producing agent.

21. The method of claim 18, wherein said bilayer-associated material includes said non-phospholipid material of said carrier vesicle.

22. The method of claim 18, wherein said bilayer-associated material includes a protein or a fragment or derivative thereof inserted into said bilayer.

23. The method of claim 18, wherein said carrier vesicle further comprises a targeting molecule and said step of delivering said carrier vesicle to a location proximate to the cell comprises delivering said carrier vesicle to a location proximate to said cell and allowing said targeting molecule to seek said cell.

24. The method of claim 23, wherein said targeting molecule is an antibody.

25. The method of claim 23, wherein said targeting molecule is a viral protein.

26. The method of claim 23, wherein said targeting molecule is a ligand for a receptor on said cell.

27. A method of transmitting a biologically active material to a cell in vitro, comprising the steps of:

(a) forming a carrier vesicle having about 2–10 lipid bilayers encapsulating said biologically active material, said carrier vesicle being in the form of a paucilamellar lipid vesicle having a non-phospholipid material as the primary structural lipid in said lipid bilayers, wherein said non-phospholipid material is a polyoxyethylene fatty acid ether that forms vesicles which fuse with cells without lysing cells upon contact with cells;

(b) delivering said carrier vesicle containing said biologically active material to a location proximate to said cell in vitro;

(c) allowing said lipid bilayer of said carrier vesicle and the membrane of said cell to fuse; and (d) allowing said biologically active material to diffuse into said cell.

28. The method of claim 27, wherein said lipid bilayer further comprises a phospholipid.

29. A method of transmitting a bilayer-associated material to a cell in vitro, comprising the steps of:

(a) forming a carrier vesicle having about 2–10 lipid bilayers incorporating said bilayer-associated material, said carrier vesicle being in the form of a paucilamellar lipid vesicle having a non-phospholipid material as the primary structural lipid in said lipid bilayers, wherein said non-phospholipid material is a polyoxyethylene fatty acid ether that forms vesicles which fuse with cells without lysing cells upon contact with cells;

(b) delivering said carrier vesicle incorporating said bilayer-associated material to a location proximate to said cell in vitro;

(c) allowing said lipid bilayer of said carrier vesicle and the membrane of said cell to fuse; and (d) allowing said bilayer-associated material to be transmitted to the membrane of said cell.

30. The method of claim 29, wherein said lipid bilayer further comprises a phospholipid.

* * * * *